(12) United States Patent
Ramos et al.

(10) Patent No.: US 11,035,105 B2
(45) Date of Patent: Jun. 15, 2021

(54) WATER QUALITY MAINTENANCE SYSTEMS

(71) Applicant: Lead Out Manufacturing, LLC, McFarland, WI (US)

(72) Inventors: Michael A. Ramos, McFarland, WI (US); Robert M. Christlieb, McFarland, WI (US)

(73) Assignee: Lead Out Manufacturing, LLC, McFarland, WI (US)

(*) Notice: Subject to any disclaimer, the term of this patent is extended or adjusted under 35 U.S.C. 154(b) by 0 days.

(21) Appl. No.: 15/845,865

(22) Filed: Dec. 18, 2017

(65) Prior Publication Data

US 2018/0171607 A1 Jun. 21, 2018

Related U.S. Application Data

(60) Provisional application No. 62/498,122, filed on Dec. 16, 2016.

(51) Int. Cl.
| | | |
|---|---|---|
| *E03B 7/07* | (2006.01) |
| *E03C 1/10* | (2006.01) |
| *G01N 33/18* | (2006.01) |
| *E03C 1/05* | (2006.01) |
| *E03B 7/08* | (2006.01) |
| *E03C 1/126* | (2006.01) |
| *E03B 7/04* | (2006.01) |
| *E03C 1/02* | (2006.01) |

(52) U.S. Cl.
CPC .............. *E03B 7/071* (2013.01); *E03B 7/045* (2013.01); *E03B 7/08* (2013.01); *E03C 1/057* (2013.01); *E03C 1/10* (2013.01); *E03C 1/126* (2013.01); *G01N 33/18* (2013.01); *E03C 2001/026* (2013.01); *Y10T 137/0324* (2015.04); *Y10T 137/6497* (2015.04)

(58) Field of Classification Search
CPC ...... E03C 1/10; E03C 1/126; Y10T 137/0324; Y10T 137/6497; E03B 7/071; E03B 7/045; E03B 7/08; G01N 33/18
See application file for complete search history.

(56) References Cited

U.S. PATENT DOCUMENTS

2004/0060602 A1* 4/2004 Mullins ................. B01D 61/12
137/551
2009/0123340 A1* 5/2009 Knudsen ................ G08B 21/12
422/105

(Continued)

OTHER PUBLICATIONS

"Mitigation Strategies for Lead Found in School Drinking Water." Illinois Department of Public Health May 9, 2017.

(Continued)

*Primary Examiner* — Atif H Chaudry
(74) *Attorney, Agent, or Firm* — Quarles & Brady LLP

(57) ABSTRACT

Water quality maintenance system are disclosed herein. The systems are configured to automatically switch between an open state allowing for purging of water from a water line and a closed state preventing water flow. The systems comprise a controller is configured to automatically generate a control signal and a purge valve comprising an electromagnetic actuator in electromechanical communication with the controller. Also disclosed herein are fixtures comprising the systems and methods of using the systems.

16 Claims, 5 Drawing Sheets

(56) References Cited

U.S. PATENT DOCUMENTS

| | | | |
|---|---|---|---|
| 2011/0303310 A1* | 12/2011 | Klicpera | B05B 12/008 137/551 |
| 2012/0004778 A1* | 1/2012 | Lai | E03B 7/045 700/282 |
| 2014/0000724 A1* | 1/2014 | Park | E03B 7/08 137/78.1 |
| 2015/0159887 A1* | 6/2015 | Kadah | F24D 19/1084 700/276 |

OTHER PUBLICATIONS

"3 Ts for Reducing Lead in Drinking Water in Schools." United States Environmental Protection Agency Oct. 2006.
"Water" Centers for Disease Control and Prevention https://www.cdc.gov/nceh/lead/tips/water.htm_Feb. 18, 2016.

* cited by examiner

WATER QUALITY MAINTENANCE SYSTEMS

CROSS-REFERENCE TO RELATED APPLICATIONS

This application claims benefit of priority to U.S. Provisional Application No. 62/498,122, filed 16 Dec. 2016, the contents of which is incorporated herein by reference in its entirety.

FIELD OF INVENTION

The present technology is generally related to water quality maintenance systems. More particularly, the present technology is related to water quality maintenance systems for automatically purging contaminants from water lines and plumbing fixtures.

BACKGROUND

Due to aging infrastructure and allowed plumbing materials, every plumbing system, plant, and fixture has some lead. Before 1993, the maximum allowable lead level for plumbing components was a weighted average of 8.75% lead on wetted surfaces of pipes, pipe fittings, plumbing fittings, and fixtures. Modern regulations still allow up to 0.25% lead.

Lead and other contaminants leech into potable water as a matter of course. The concentration of lead and other contaminants in water depend on the level of contaminants in the system and the contact time between water and the plumbing line and fixture. Stagnation of water within plumbing lines and fixtures leads to elevated contaminant levels. As a result, there is a risk of lead or other contaminants being present in harmful concentrations regardless of whether the building or its plumbing system is new or old.

It is therefore necessary to mitigate the harmful effects of lead and other contaminants in drinking water through the use of water quality maintenance systems.

SUMMARY OF THE INVENTION

Disclosed herein are water quality maintenance systems. The systems are configured to automatically switch between an open state allowing for purging of water from a water line and a closed state preventing water flow. The systems may comprise a controller is configured to automatically generate a control signal and a purge valve comprising an electromagnetic actuator in electromechanical communication with the controller. In some embodiments, the controller comprises an electronic circuit configured to execute a set of instructions for automatically generating the control signal, and memory for storing the set of instructions. The system may further comprising a relay in electrical communication with the controller and positioned in a circuit with the purge valve configured to receive the control signal and switch the circuit between an open circuit and a closed circuit. The system may also comprise a power supply for driving the purge valve, a power supply for driving the controller, a sensor, an input/output device, a time, or any combination thereof.

Another aspect of the invention is plumbing fixtures comprising the systems. The fixture may comprise a water line, the water line comprising an inlet and outlet for providing water; a purge valve comprising an electromagnetic actuator interposed in the water line between the inlet and outlet, and a controller in communication with the purge valve configured to automatically generate a control signal for the automatic purging of the water line. In some embodiments, the water line comprises two parallel water lines between the inlet and the outlet, the purge valve is interposed in one of the parallel water lines, and a manually operated valve is interposed in the other water line. In some embodiments, the fixture is a faucet, a sink, or a drinking fountain.

Another aspect of the invention is a method for automatic water quality maintenance. The method may comprise: executing a set of instructions with a controller to automatically generate a control sign; communicating the control signal to a purge valve; and switching the purge valve from a closed state preventing water flow to an open state allowing for purging of a water line. The method may further comprise installing a water quality maintenance system configured to automatically switch between an open state allowing for purging of water from a water line and a closed state preventing water flow. The method may further comprise receiving sensory input from a sensor, timing input from a timer, or an information input from an input/output device.

DETAILED DESCRIPTION OF THE INVENTION

The technology disclosed herein is a low cost water quality maintenance system, fixtures incorporating the systems, and methods for using the systems that ensure that cold, clean water is available at any time. The systems described herein automatically purge water lines and fixtures to ensure that contaminant concentrations are within acceptable tolerances in an effective, efficient, and proscribed manner without any additional labor resources required. As a result, stagnant water within the water lines and fixtures having elevated contaminant levels can be flushed, reducing contaminant levels into an acceptable range. The system also offers a flexible platform that can automatically adjust to changes in water usage as well as water quality. The system may be used in any residential or public building, including houses, apartments, hotels, schools, day care centers, hospitals, or transportation centers such as airports, train stations, and bus stations.

The system combats harmful concentrations of contaminants by purging sediment and stagnant water on a predetermined or automatically adjustable schedule without human intervention. As a result, the system ensures that water provided from an outlet, e.g., faucet or spigot, has not endured prolonged periods of stagnation.

Moreover, the system combats harmful concentrations of contaminants by increasing the availability of phosphates. Phosphates, such as orthophosphate and polyphosphates are added by municipal water systems for the express purpose of inhibiting corrosion of water lines by sequestering metals, including lead, and forming a corrosion inhibiting coating that seals the interior of plumbing systems. Purging the system ensures that phosphates are available to perform their essential metal sequestering and coating functions.

Figure 1A:
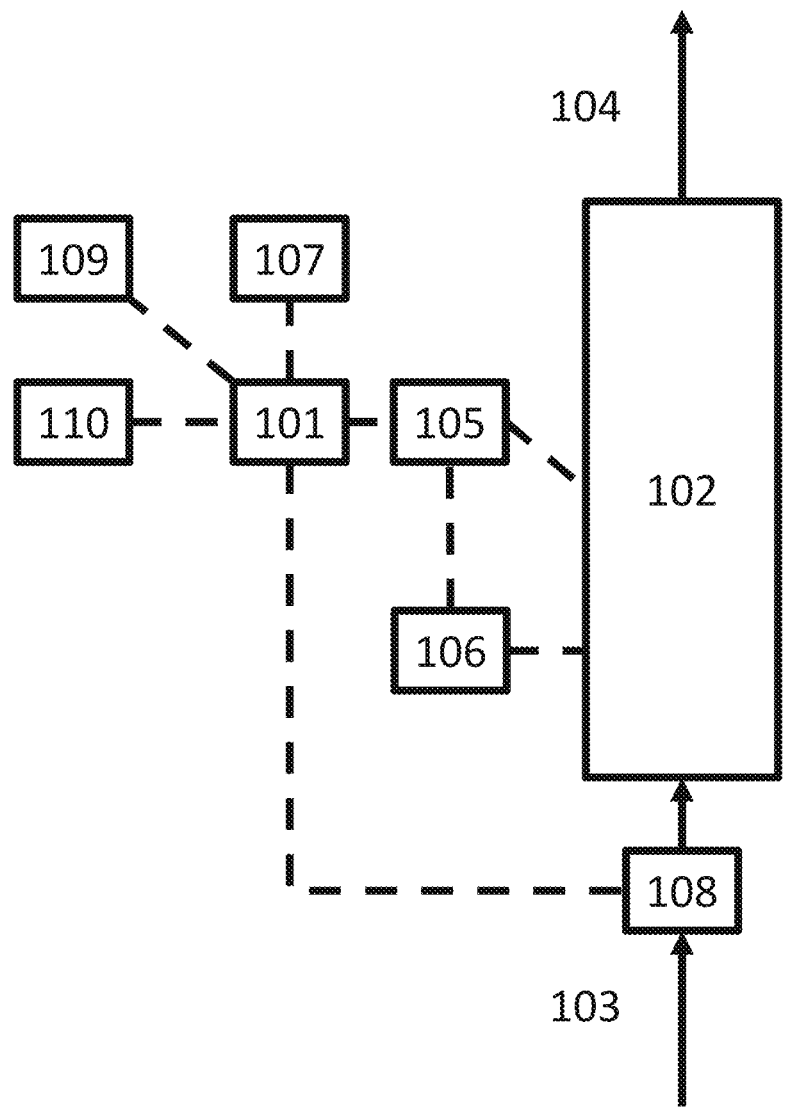
FIG. 1A illustrates an exemplary embodiment of a water quality maintenance system.
Figure 1B:
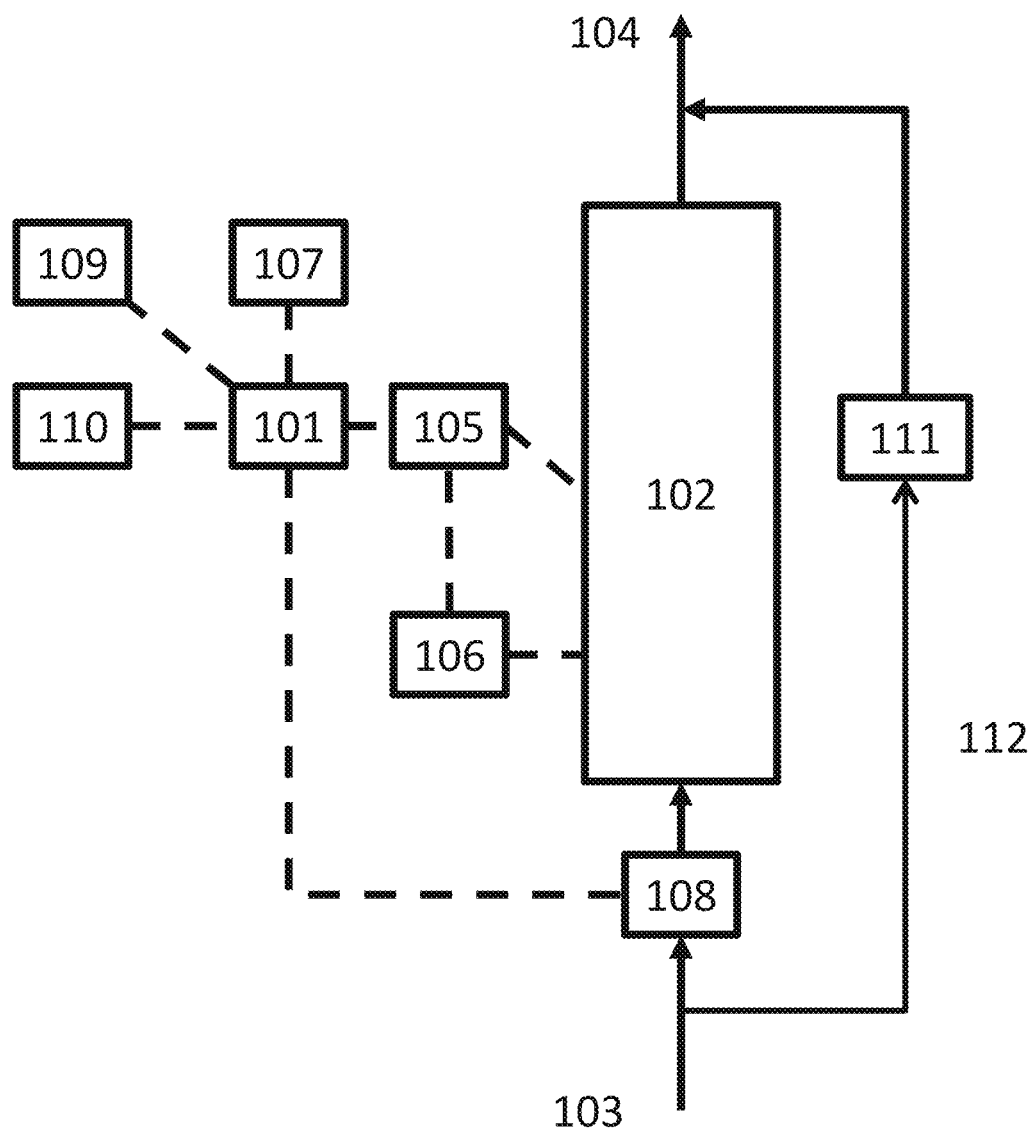
FIG. 1B illustrates an exemplary embodiment of a water quality maintenance system.

FIGS. 1A and 1B illustrate exemplary embodiments of the invention. The water quality maintenance system comprises a controller 101 and a purge valve 102. The purge valve is interposed in a water line (depicted with the solid arrow) between an inlet 103 and an outlet 104 for providing water. The controller 101 and the purge valve 102 are in electro-mechanical communication (depicted with dashed lined), and the controller 101 is configured to automatically generate a control signal that results in the purge valve switching between an open state allowing for purging of water and a closed state preventing flow. As used herein, electromagnetic communication may be any wired or wireless means of communicating with electricity, magnetism, or electromagnetic waves. When the purge valve 102 is in the open state the water line is flushed and the concentration of contaminants is reduced.

The controller 101 may be any suitable device for automatically generating the control signal. In some embodiments, the controller comprises a processor configured to execute a set of instructions for automatically generating the control signal. The processor may be any of the various processors comprising an integrated circuit. In particular embodiments, the controller is a microcontroller comprising a processor, memory for storing the set of instructions, and peripheral interfaces integrated into a single device. Those of skill in the art will appreciate that many different types of controllers in various configurations may be suitable for automatically generating the control signal and integration with the system described herein.

The set of instructions for automatically generating control signal can vary widely depending on wide variety of parameters. For example, the set of instructions can be tailored by for the municipal water quality, the location of the building, the location of the installed water quality maintenance system within the building, the number of installed water quality maintenance system within the building, the size of the building, the age of building, type of fixture, typical building or fixture usage, or affected population.

The purge valve 102 may be any valve capable of responding to the control signal and switching between the open state and the closed state. In some embodiments, the purge valve comprises an electromagnetic actuator that switches the purge valve between the open and closed configurations. In particular embodiments, the purge valve is a solenoid valve. Those of skill in the art will appreciate that many different types of purge valves may be suitable use with the system described herein.

The controller 101 and the purge valve 102 may be in electromagnetic communication via a relay 105. When a relay 105 is used to communicate the control signal between the control 101 and the purge valve 102, the relay 105 is positioned along a circuit with the purge valve 102 and a power supply 106 that provides the electromotive driving force to switch the purge valve 102 between the open and closed states. The control signal may be used to switch the relay 105 between open and closed circuit configurations such that when the circuit is closed the power supply 106 can drive switching in the purge valve.

The controller 101 may be configured to interface with various peripherals. Examples of peripherals for use with the system include sensors, input/output devices, timers, or any combination thereof. As used herein, combinations include two or more peripherals within a particular or between different peripheral classes.

A timer 107 may be interfaced with the controller 101. The timer may be any suitable timer for tracking time intervals. This includes, for example, crystal timers. The timer may be integrated with the controller or external to the controller. The timer may be used to track any number of timings that could be associated with the water line purging, including time between open purge valve states and/or open and closed purge valve states. This timing information may be communicated to the controller and used to update a set of instructions and/or used to determine when to purge the water line.

Sensors for use with the system may be any sensor capable of providing sensory inputs for the controller to determine when to automatically generate a control signal or for updating the set of instructions for automatically generating a control signal. In some embodiments, the sensor may be a water-quality sensor, an environmental sensor, or both.

A water-quality sensor 108 may be configured to detect one of more properties of the water within the water line. The property of interest may be communicated to the controller and used to update set of instructions and/or used to determine when to purge the water line. The water-quality sensor 108 may be positioned before the purge valve (as shown in FIGS. 1A and 1B), after the purge valve, integrated with the purge valve, or any combination thereof. In some embodiments, the property detected is the temperature of the water, the flow rate of the water, analyte concentration, or any combination thereof. Analytes of interest may include, without limitation, lead, phosphates (including orthophosphates or polyphosphates), oxygen, chloride, or any combination thereof.

An environmental sensor 109 may be configured to detect one or more properties of the environment where the system is located. The property of interest may be communicated to the controller and used to update a set of instructions and/or used to determine when to purge the water line. The environmental sensor may be positioned in any suitable place for detecting the property of interest. Examples of environmental sensors include electrical switches, light sensors, touch sensors, motion sensors, infrared sensors, or any combination thereof. In some cases the environmental property of interest may be the proximity of a human. In other cases, the environmental property of interest may be a specific human action. An example of a specific human action may be an action typically used to activate a hands-free faucet or spigot. Being able to detect such an environmental property would allow the system to be manually operated.

The input/output device 110 may be interfaced with the controller 101. Input/output devices may be any device configured to facilitate the transmission of information from the controller to an external device and/or receipt of information by the controller from an external device. Information received may be used by the controller to determine when to generate a control signal or to update a set of instructions. Information transmitted from the controller may be used in a number of ways, including for monitoring system operation or water quality. The external device may be a processor capable of receiving the information, processing the information and/or a set of instructions, and transmitting information back to the controller. The information received by the controller may be used to determine when to automatically generate the control signal and/or update the set of instructions. Examples of input/output devices include, without limitation, a universal serial bus, a network interface controller, any input/output device normally associated with a processor, or any combination thereof. In some embodiments, the network interface controller is a wireless network interface face controller that may use 802.11 protocols (e.g., Wi-Fi protocols) or non-802.11 protocols (e.g., Bluetooth protocols).

The systems described herein may be integrated with a plumbing fixture or retrofit into existing plumbing infrastructure. The fixture may be any suitable plumbing fixture having an outlet and a drain, e.g., a sink or drinking fountain, or any component of such a fixture, e.g., a faucet or spigot.

Retrofitting may be accomplished by splitting the water line into two parallel water lines as illustrated in FIG. 1B. The purge valve 102 may be interposed in a first water line and a second valve 111 may be interposed in a second water line 112 between the inlet 103 and the outlet 104. The second valve 111 may be a manually controlled valve for the fixture. This allows for normal use of existing fixtures of plumbing infrastructure as well as automatic purging for maintaining water quality.

Methods for automatic water quality maintenance comprising providing a set of instructions for automatically generating a control signal; executing the set of instructions with a controller to automatically generate a control sign; communicating the control signal to a purge valve; and switching the purge valve from a closed state preventing water flow to an open state allowing for purging of a water line.

Figure 2A:
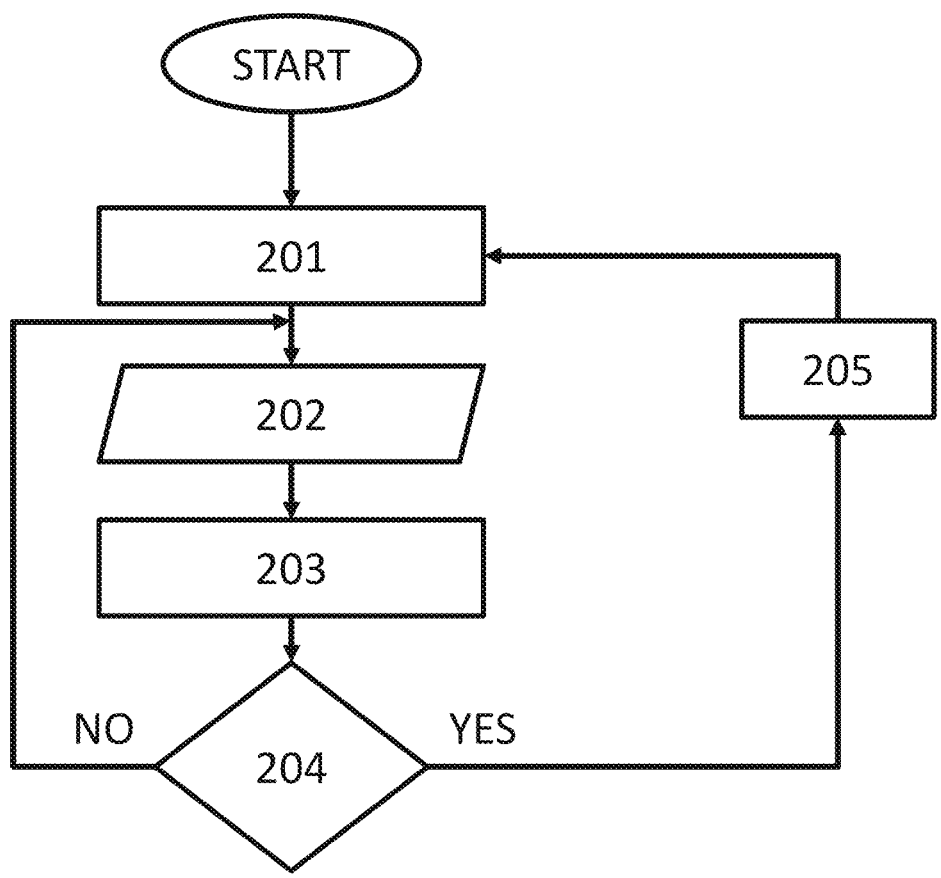
FIG. 2A illustrates an exemplary method of using the water quality maintenance system.

An embodiment of the method is illustrated in in FIG. 2A. The method may be started by providing the system described herein integrated with a water line. The method may comprise an initialization step 201 that provides a set of instructions to automatically generate the control signal by the controller. The set of instructions may be stored in permanent memory integrated with the controller, provided through an input/output device, or a previously used set of instructions. The method may further comprise an input step 202 that allows the controller to receive an input. The input may be sensory input from a sensor, an information input from an input/output device, a timing input from a timer, or any combination thereof. The controller may use any input received in an update step 203 that allows for an updated set of instructions to be provided from an external device or processed by the controller. In a purge determination step 204 the controller determines whether a control signal should be generated. If the control signal is generated, a purge step 205 is executed and the instructions are reinitialized 201. If the control signal is not generated, the cycle is repeated with a new input step.

An exemplary illustration of the method described above is provided where the automatic purging of the system is determined by timing inputs. The initialization step 201 may comprise providing a set of instructions to automatically generate a control signal for purging on a periodic schedule. For example, the instructions may be to purge the line for 1 minute every hour, 2 minutes every 2 hours, or 3 minutes every 3 hours. Other periodic purging instructions can be provided and tailored to needs of an individual building or fixture. The input step 202 may comprise receiving a timing input from a timer. An example may be an electrical impulse generated by a crystal timer. The update step 203 may comprise updating a counter based on the controller receiving the electrical impulse generated by a crystal timer. The determination step 204 allows for the controller to compare the counter to a set of logic instructions to determine whether the purge value should be open or closed. For a set of instructions providing for purging 1 minute every hour, the control signal may open the valve for the first minute of the hour and close the valve for the remaining 59 minutes of the hour.

An exemplary illustration of the method described above is provided where the automatic purging of the system is determined by timing input as well as sensory inputs. The initialization step 201 may comprise providing a set of instructions to automatically generate a control signal for periodic purging provided there is some indication of human proximity. An example of human proximity may be when lights are turned on. Instructions of this sort may be to purge for 10 minutes after the lights are turned and for 3 minutes every three hours so long as the lights are still on or for 20 minutes after the lights are turned on and for 3 minutes every hour so long as the lights are still on. The input step 202 may comprise receiving a timing input from a timer and a sensory input from a light sensor or an ammeter tied into a lighting circuit. The update step 203 may comprise updating a counter based on the controller receiving the electrical impulse generated by a crystal timer which was initialized by the sensory input. The determination step 204 allows for the controller to compare the counter to a set of logic instructions to determine whether the purge value should be open or closed. Other purging instructions can be provided and tailored to needs of an individual building or fixture.

Figure 2B:
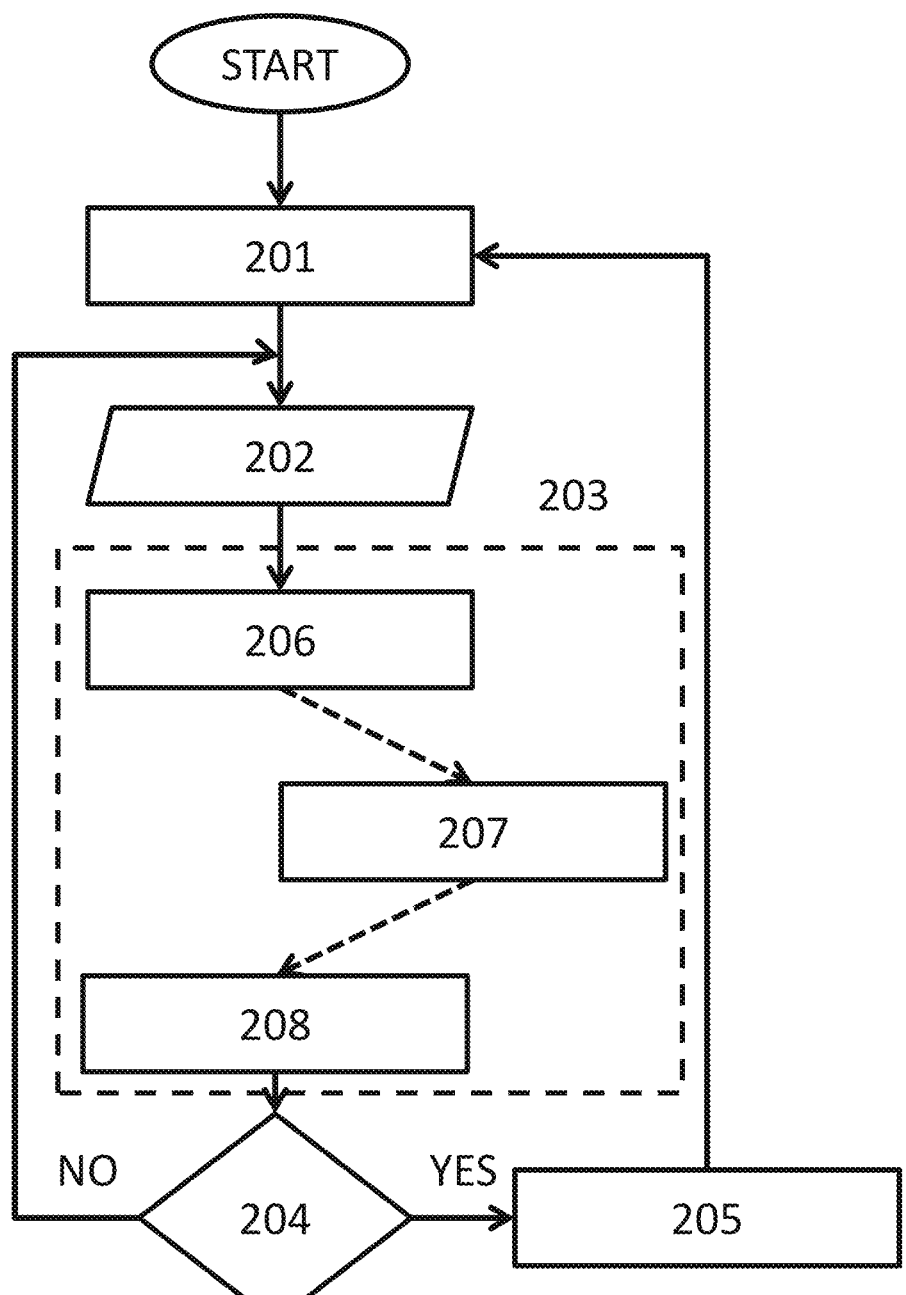
FIG. 2B illustrates an exemplary method of using the water quality maintenance system.

Another embodiment of the method is illustrated in FIG. 2B. FIG. 2B differs from FIG. 2A in the update step 203 (bounded box). The update step 203 further comprises a transmitting step 206 from an input/output device of the system to an external device, an updating step 207 performed by an external device, and a receiving step 208 from the external device to an input/output device of the system. The controller receives the information from the external device to determine whether the control signal should be generated 204.

EXAMPLES

Example 1

Figure 3:
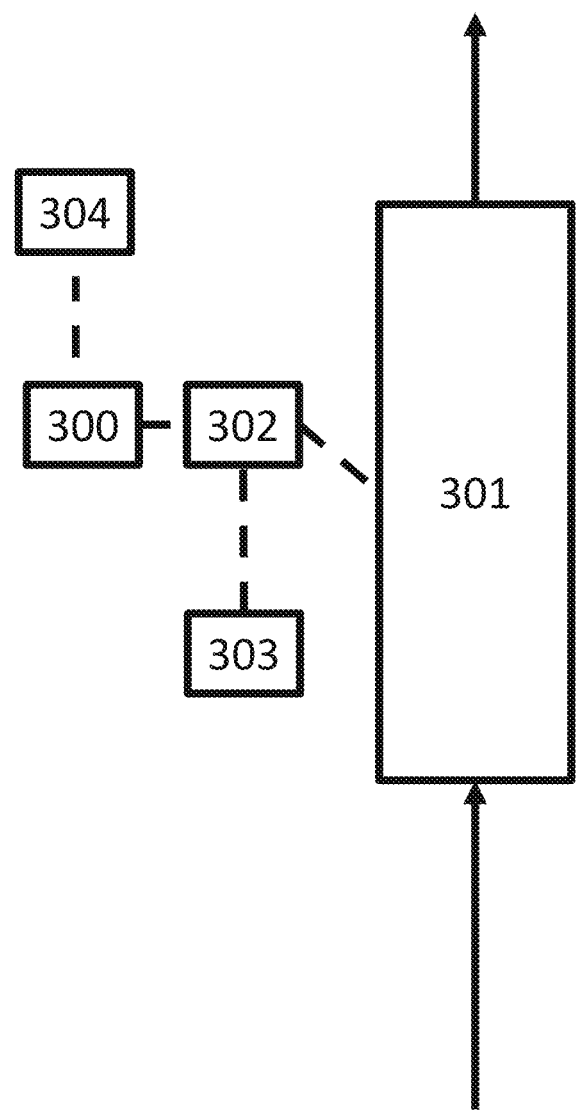
FIG. 3 illustrates an exemplary embodiment of using the water quality maintenance system.

A water-quality maintenance system was prepared from microcontroller with integrated timer (Keyestudio UNO) 300, a solenoid valve (U.S. Solid) 301, a relay module 302, a 12 V DC power supply 303, and a 5 V DC power supply 304. See, FIG. 3. The relay was connected to the solenoid valve and 12 V DC power supply via the normally open connection to form a circuit. The relay was also to the 5 V DC interface, ground, and digital pin #4 on the board of the controller. The controller was provided instructions to purge the line every 1 hour for 3 minutes in duration.

Those of skill in the art will appreciate that many different components may be used to build the system and may different sets of instruction may be provided.

Example 2

A water-quality maintenance system was prepared according to Example 1 with the addition of a sensor for detecting when lights are turned on. The controller was provided instructions to purge when the lights were turned out and then every 3 hours thereafter until the lights were turned off.

Those of skill in the art will appreciate that many different components may be used to build the system and may different sets of instruction may be provided.

Example 3

The water quality maintenance systems of the present invention effectively mitigate lead. The present example demonstrates that it is possible to install water quality maintenance systems to maintain non-detectable (i.e., <2 ppb) levels in all potable water sources within a Chicago-area high school comprising 248,453 square feet serving over 1700 students and built in 1930. The building has a total of 42 drinking fountains clustered in clustered locations through 4 student-occupied floors.

An embodiment of the water quality maintenance system was first install at the 1st Floor NW1 location to demonstrate proof of concept. Testing has since expanded to automate flushing of 6 of 6 risers as well as the main in the basement. Strategically placed bottle fillers are also a component of the flushing system as they are found to stimulate usage on key risers in conjunction with the installed water quality maintenance systems.

Focusing first on the main, simulated or boosted, fresh water supplied to all risers. This shortened the distance the drinking fountains above must pull to get fresh water while leveraging existing infrastructure. The water quality maintenance system was initially instructed to flush the volume of the water main every three hours with a run time of 1.5 hours to flush the pipe.

Water-fountain installed water quality maintenance systems were initially instructed to flush for 20 mins at the start of the day when the lights were turned on and 5 minutes per hour thereafter as long as the lights were on.

The last riser added is located in the south wing, southeast corner and services only drinking fountains on floors 1-3. These 6 drinking fountains are the least used in the school. After removal of the rust particles clogging the base of the drain and a week of automated flushing service, the riser has stabilized and is consistent with other fixtures being flushed.

Table 1 shows the detected lead levels at the clustered water fountains before and after installation of water quality maintenance systems throughout the building.

TABLE 1

Detected lead levels in water fixtures

| Location | Installed | Before (Pb ppb) | After (Pb ppb) |
|---|---|---|---|
| 4th Floor North | Yes | ND | ND |
| 4th Floor South | No | ND | ND |
| 3rd Floor NE | Yes | ND | ND |
| 3rd Floor NW1 | Bottle Filler | ND | ND |
| 3rd Floor NW2 | No | ND | NT |
| 3rd Floor SW2 | No | ND | ND |
| 3rd Floor SW1 | No | ND | ND |
| 3rd Floor SE | Yes | BA | ND |
| 2nd Floor NE | No | BA | ND |
| 2nd Floor NW1 | No | ND | ND |
| 2nd Floor NW2 | No | ND | ND |
| 2nd Floor SW2 | No | ND | ND |
| 2nd Floor SW1 | Bottle Filler | ND | NT |
| 2nd Floor SE | No | AA | ND |
| 1st Floor NE | No | ND | ND |
| 1st Floor NW1 | Yes | BA | ND |
| 1st Floor NW2 | No | AA | ND |
| 1st Floor SW2 | No | ND | ND |
| 1st Floor SW1 | No | ND | ND |
| 1st Floor SE | No | ND | ND |
| Main | Yes | NT | ND |

ND: Not dectectable (<2 ppb)
BA: Below actionable level (2-15 ppb)
AA: Above actionable level (>15 ppb)
NT: Not tested Key findings from the installation of water quality maintenance systems: First, all drinking fountains are testing below ND at <2 ppb that are being serviced by a water quality maintenance system. Second, stagnation time is limited to less than hour in the morning. Third, once flushing was applied to a riser, the riser tended to stabilize in 5 to 10 days. Finally, installation of water quality maintenance systems assists in maintaining contaminant levels below detectable levels at a fixture even when the system is not directly associated with the fixture. This effect is improved by flushing at or near the main or near the top of a riser.

The invention claimed is:

1. A water quality maintenance system configured to automatically switch between an open state allowing for purging of water from a water line and a closed state preventing water flow, the system comprising:
   (a) a controller is configured to automatically generate a periodic control signal;
   (b) a purge valve comprising an electromagnetic actuator in electromechanical communication with the controller;
   (c) a relay in electrical communication with the controller and positioned in a circuit with the purge valve;
   (d) a temperature sensor;
   (e) a flow meter;
   (f) an analyte sensor;
   (g) an input/output device; and
   (h) an environmental sensor, wherein the environmental sensor is a light sensor,
   wherein the controller comprises:
      (i) an electronic circuit configured to receive an input from each of the environmental sensor, the temperature sensor, the flow meter, the analyte sensor, and the input/output device, update a set of instructions for automatically generating the control signal when the light sensor provides an input that a light has been turned on, and execute the updated set of instructions, and
      (ii) memory for storing the set of instructions for generating the control signal for purging water from the water line,
   wherein the system is integrated with a plumbing fixture, and
   wherein the relay is configured to receive the control signal and switch the circuit between an open circuit and a closed circuit for periodically purging water from the plumbing fixture while the light is turned on.

2. The system of claim 1 further comprising a power supply for driving the purge valve.

3. The system of claim 1 further comprising a power supply for driving the controller.

4. The system of claim 1, wherein the analyte is lead, phosphate, oxygen, chloride, or any combination thereof.

5. The system of claim 1, wherein the environmental sensor further comprises a touch sensor, a motion sensor, an IR sensor, or any combination thereof.

6. The system of claim 1, wherein the input/output device is a universal serial bus, a network interface controller, or any combination thereof.

7. The system of claim 6, wherein the network interface controller is a wireless network interface controller.

8. The system of claim 1 further comprising a timer.

9. A method for automatic water quality maintenance, the method comprising:
   (a) receiving an input from the light sensor of the system of claim 1;
   (b) providing the input to a controller;
   (c) executing the updated set of instructions with the controller to automatically generate a periodic control signal for purging water from the plumbing fixture;
   (d) communicating the control signal to a purge valve; and (e) switching periodically the purge valve from a closed state preventing water flow to an open state allowing for purging of the plumbing fixture while the light is turned on.

10. The method of claim 9 further comprising installing the water quality maintenance system configured to automatically switch between an open state allowing for purging of water from a water line and a closed state preventing water flow.

11. The method of claim 9 further comprising providing a second input to the controller, wherein the second input is a sensory input from the temperature sensor, the flow meter, or the analyte sensor or an information input from an input/output device.

12. The method of claim 11, wherein the sensory input is an analyte concentration.

13. The method of claim 12, wherein the analyte concentration is a concentration of lead, phosphate, oxygen, chloride, or any combination thereof.

14. A plumbing fixture for automatic water quality maintenance, the fixture comprising:
(a) a water line, the water line comprising an inlet and outlet for providing water;
(b) a purge valve comprising an electromagnetic actuator interposed in the water line between the inlet and outlet;
(c) a controller in communication with the purge valve,
(d) a relay in electrical communication with the controller and positioned in a circuit with the purge valve;
(e) a temperature sensor;
(f) a flow meter;
(g) an analyte sensor;
(h) an input/output device; and
(i) an environmental sensor, wherein the environmental sensor is a light sensor,
wherein the controller is configured to receive an input from each of the environmental sensor, the temperature sensor, the flow meter, the analyte sensor, and the input/output device, update a set of instructions for automatically generating a control signal when the light sensor provides an input that a light has been turned on for the automatic and periodic purging of the plumbing fixture while the light is turned on, and execute the updated set of instructions for generating the control signal for purging water from the plumbing fixture.

15. The fixture of claim 14, wherein the water line comprises two parallel water lines between the inlet and the outlet, the purge valve is interposed in one of the parallel water lines, and a manually operated valve is interposed in the other water line.

16. The fixture of claim 14, wherein the fixture is a faucet, a sink, or a drinking fountain.

* * * * *